United States Patent [19]
Wijeratne et al.

[11] Patent Number: 6,036,670
[45] Date of Patent: *Mar. 14, 2000

[54] COILED TRANSITION BALLOON CATHETER, ASSEMBLY AND PROCEDURE

[75] Inventors: Lalith Hiran Wijeratne, Cooper City; Luis Alberto Davila, Coral Springs; Marco Aurelio Nino, Miami, all of Fla.

[73] Assignee: Cordis Corporation, Miami, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/996,608

[22] Filed: Dec. 23, 1997

[51] Int. Cl.[7] .................................................. A61M 29/00
[52] U.S. Cl. ............................................. 604/96; 604/526
[58] Field of Search ............................ 604/96, 523, 524, 604/525, 526, 530, 532, 533, 500, 508, 509

[56] References Cited

U.S. PATENT DOCUMENTS

| | | |
|---|---|---|
| 4,762,129 | 8/1988 | Bonzel . |
| 5,040,548 | 8/1991 | Yock . |
| 5,061,273 | 10/1991 | Yock . |
| 5,300,025 | 4/1994 | Wantick ..................................... 604/96 |
| 5,346,505 | 9/1994 | Leopold . |
| 5,458,605 | 10/1995 | Klemm ................................ 604/526 X |
| 5,782,809 | 7/1998 | Umeno et al. .......................... 604/526 |
| 5,797,874 | 8/1998 | Spears .................................. 604/526 X |
| 5,807,355 | 9/1998 | Ramzipoor et al. ................... 604/96 X |

*Primary Examiner*—John D. Yasko
*Attorney, Agent, or Firm*—Cook, Alex, McFarron Manzo, Cummings & Mehler, Ltd.

[57] ABSTRACT

A balloon dilatation catheter is provided which has a stiff proximal cannula made of a material such as metal hypotubing. The distal end of the catheter includes an inflatable medical device balloon, an inflation lumen and a guidewire lumen. A coiled transition assembly is positioned between the proximal cannula and the distal end section. This coiled transition assembly has a tightly wound coil within a tube and provides for a flexible transition between the two components of diverse stiffness, namely the proximal cannula and the flexible distal end portion. The dilatation catheter typically has an easily or rapidly exchangeable feature and is used in conjunction with a guiding catheter. During a procedure when the catheters are within the vascular system, the coiled transition section of the dilatation catheter readily follows tightly curved portions of the inserted guiding catheterby.

29 Claims, 1 Drawing Sheet

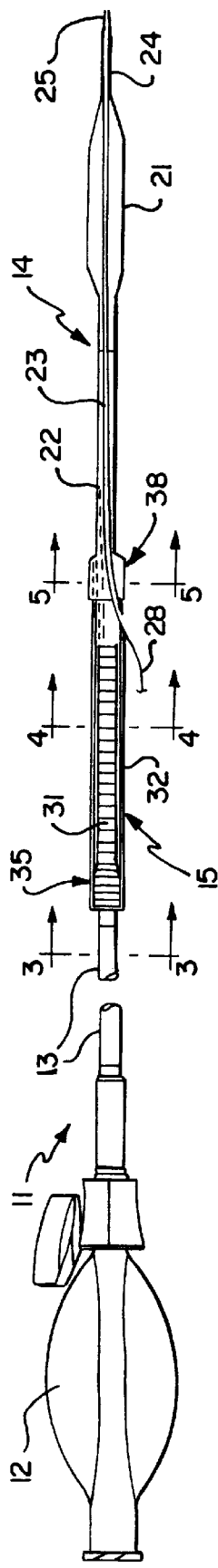
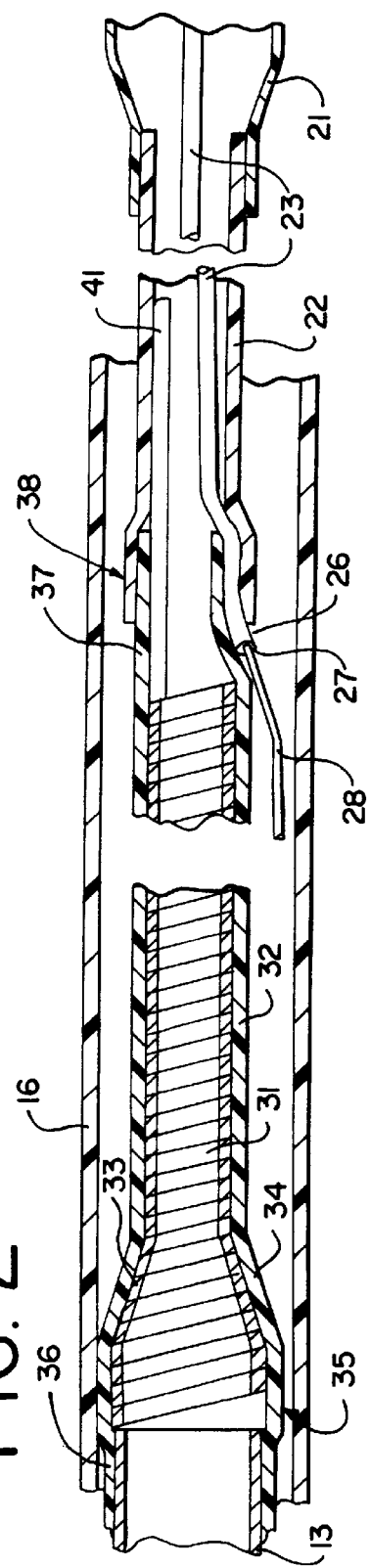
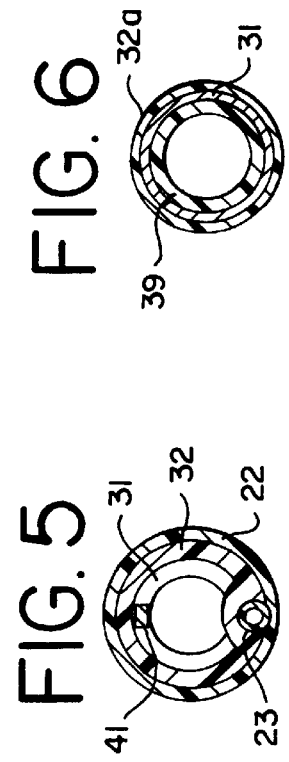
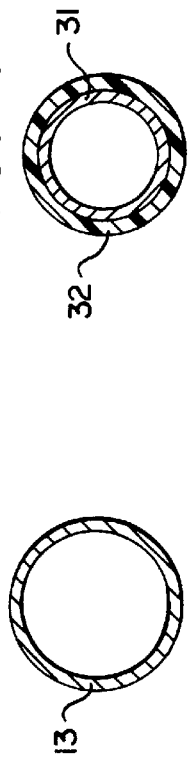

COILED TRANSITION BALLOON CATHETER, ASSEMBLY AND PROCEDURE

BACKGROUND OF THE INVENTION

The present invention generally relates to a balloon catheter for conducting dilatation procedures within the vascular system and in conjunction with a guiding catheter within which the balloon catheter is slidably moved for positioning and treatment. The balloon catheter incorporates an elongated, high-strength cannula as its proximal tube component and has a distal end assembly which incorporates the balloon and which has a flexibility substantially greater than that of the proximal cannula. The proximal cannula and the distal end assembly are joined together by a transition assembly which includes an elongated coil. When negotiating a tight curve during a medical procedure using the catheter system, the coil imparts a force on the guiding catheter which is relatively low so as to avoid unintentional dislodgement of the guiding catheter from its intended position, such as in the atrium of the heart.

In many applications for dilatation catheters, it is important to provide a proximal catheter tube which is relatively stiff and of high strength so that the elongated proximal tube accepts and transmits column forces, as well as torsional forces, from the proximal end of the catheter which remains outside of the body and to the distal end portion of the catheter so that the latter is properly positioned for effecting the dilatation procedure. Proximal elongated tubes such as metal hypotubes have been proposed or used in the past. This type of stiff tubing does not extend the full length of the balloon catheter. In order to maneuver through tight turns and/or constricting passageways, the distal end portion of the catheter must be quite flexible.

While the objective of having a stiff proximal hypotube and a flexible distal portion has been a desirable objective, achieving this objective is complicated by the need for providing a suitable transition between a very stiff elongated member and a very flexible elongated member. It has been found that, when two such diverse stiffness sections interface directly with each other, there is a strong tendency that the catheter will prolapse on itself during movement, especially in the distal direction, of the balloon catheter with respect to the guiding catheter. Among other concerns, this type of action will mean that the balloon catheter does not move consistently smoothly through the guiding catheter. At times, this can result in guiding catheter dislodgement from its desired position within the vascular system of the body, such as in the atrium of the heart.

In the past, catheters of this general type have included a transitional section between a stiff hypotube type of component and a flexible distal end portion of the catheter. A primary component of these types of transitional section approaches is the incorporation of a rigid structure generally at the transition location, whereby the stiffness of the proximal hypotube is gradually reduced as same moves into the flexible distal portion of the catheter. In some known systems, a bridging wire is provided as a distally oriented extension of the hypotube, this being positioned within a transition section between the distal end of the hypotube and the proximal end of the distal end portion of the catheter which contains the balloon.

With approaches such as those generally identified above, the bridge wire or the like creates difficulties when the balloon catheter must be passed through a tightly curved portion of the guiding catheter. There is a strong tendency for the bridge wire to transfer a bending force to the walls of the guiding catheter, due to the stiffness of the bridging wire, which force transfer typically increases when the tightness of the curve which must be navigated increases.

There is accordingly a need for a catheter system having a balloon catheter which will easily navigate tight curves in the distal portion of the guiding catheter and without imparting undue force to the walls of the guiding catheter, which force has been known to result in unintentional dislodgement of the guiding catheter as a result of movement of the balloon catheter therewithin. In addressing this problem, the present invention concentrates on the structure of a transition section between an elongated stiff proximal tube and a flexible distal portion.

Problems to which the present invention are directed can be especially relevant in catheters which incorporate a lumen for guidewire passage which is provided only at the distal end portion of the catheter. Such an overall structure permits the physician to easily and/or rapidly exchange one balloon catheter for another and generally avoids the need for extended length or extendable length guidewires and the problems associated with providing and handling same. Balloon catheter systems of this general type are shown in Yock U.S. Pat. No. 5,061,273 and Leopold U.S. Pat. No. 5,346,505, their subject matter being incorporated hereinto by reference. Generally speaking, by providing a quidewire exit port in a generally distal portion of the catheter, this can intensify the problem of undesired weakness of the catheter caused by stiffness differences between the section of the catheter having the guidewire tube and guidewire and the section of the catheter immediately proximal of the guidewire exit port. There is accordingly a need for an improved transition structure in the vicinity of the guidewire exit port of a balloon catheter having such an easily and/or rapidly exchangeable feature.

SUMMARY OF THE INVENTION

In accordance with the present invention, a balloon dilatation catheter is provided which incorporates a coil transition assembly between an elongated, high-strength proximal cannula and a generally tubular distal end assembly which is substantially more flexible than the proximal cannula. The coil transition assembly provides flexible bending strain relief and incorporates a coil member within a transition tube. This balloon dilatation catheter is used in combination with a guiding catheter; the balloon dilatation catheter is able to smoothly follow sharp curves of the guiding catheter which are typically encountered during a dilatation procedure such as an angioplasty. With this combination, the coil transition assembly imparts a force on the guiding catheter which is so low as to avoid dislodgement of the guiding catheter from its intended position within the vascular system when the dilatation catheter is moved within the guiding catheter.

It is accordingly a general object of the present invention to provide an improved dilatation catheter, combination of dilatation catheter and guiding catheter, and procedure for effecting balloon dilatation therewith.

Another object of this invention is to provide an improved balloon catheter having a transition assembly which provides flexible bending strain relief during dilatation procedures and the like.

Another of the present invention is to provide an improved combination of balloon dilatation catheter and guiding catheter and a procedure for use thereof such that, during slidable positioning of the balloon dilatation catheter within the guiding catheter, the transition section readily bends in an arc, thereby minimizing the force applied to the guiding catheter and avoiding dislodgement of the guiding catheter from the position at which it had been set by the physician.

Another object of this invention is to provide a balloon dilatation catheter which moves linearly forwardly inside of a guiding catheter without undesired coil flexing which could hinder transmission of forces from the proximal end of the catheter which is outside of the body to the distal end of the catheter.

Another object of the present invention is to provide an improved balloon dilatation catheter and guiding catheter combination which reduces the chance of having the guiding catheter become dislodged from the atrium during an angioplasty procedure.

Another object of this invention is to provide a balloon dilatation catheter having a transition section which reduces the incidence of kinking thereat.

Another object of the present invention to provide an improved balloon dilatation catheter and guiding catheter combination which exhibits an advantageous ease of tracking and lower tracking force due to having a coil transition which forms to the shape of the guiding catheter when that transition section moves through the guiding catheter.

Another object of the present invention is to provide a transition section for a balloon dilatation catheter which provides a relatively larger cross-sectional area for passage of balloon inflation media therethrough during balloon inflation and deflation.

These and other objects, features and advantages of the present invention will be apparent from and clearly understood through a consideration of the following detailed description.

BRIEF DESCRIPTION OF THE DRAWINGS

In the course of this description, reference will be made to the attached drawings, wherein:

FIG. 1 is a partially schematic generally elevational view of a preferred balloon dilatation catheter in accordance with the present invention;

FIG. 2 is an enlarged, substantially cross-sectional view including the transition section of the catheter generally illustrated in FIG. 1, shown positioned within a guiding catheter, partially cut away and shown in cross-section;

FIG. 3 is a cross-sectional view along the line 3—3 of FIG. 1;

FIG. 4 is a cross-sectional view along the line 4—4 of FIG. 1;

FIG. 5 is a cross-sectional view along the line 5—5 of FIG. 1; and

FIG. 6 is a cross-sectional view similar to FIG. 4, but with respect to an alternative embodiment.

DESCRIPTION OF THE PREFERRED EMBODIMENTS

A preferred balloon dilatation catheter is generally designated in FIG. 1 by reference numeral 11. It includes a hub assembly 12 of generally known structure for manipulating the catheter from a location outside of the body in a manner which is generally known in the art. An elongated, high strength proximal cannula 13 is attached to the hub assembly by a suitable structure and approach. A distal end assembly, generally designated at 14, provides the distal portion of the catheter. A transition assembly, generally designated at 15, connects the flexible distal end assembly 14 to the proximal cannula 13. A guiding catheter 16 is generally depicted in FIG. 2 in sliding engagement with the balloon dilatation catheter.

With more particular reference to the proximal cannula 13, it is preferably made of a hypotube, typically made of metal. Especially stiff polymers can also be used. Hypotubes include those made of stainless steel, other stiff alloys available for use within the body, nickel-titanium alloys such as Nitinold, and the like. The proximal cannula incorporates a material and structure which provides excellent load-bearing properties, including high column strength and excellent torqueability. Properties such as these permit the physician to manipulate the substantial proximal length of the catheter while the catheter is inserted within and through the vascular system of the patient. Such a high-strength cannula also provides exceptionally responsive movement of the more distal portions of the catheter in response to movements such as twisting and short longitudinal movements in and out within the vascular system.

It will be appreciated that excellent control at this proximal portion of the balloon dilatation catheter appreciably enhances the performance characteristics of, and imparts an advantageous sure-handed feel to a balloon dilatation catheter. Typically, the length of the elongated cannula plus the hub assembly is between about 100 cm and about 120 cm. A typical balloon dilatation catheter in accordance with the invention has a total length, from the hub assembly to the distal tip of about 140 cm to about 160 cm.

Another particular advantage of making the proximal cannula of a material such as stainless steel or other metal alloy or especially strong polymer is that these materials provide high strength with a minimum of wall thickness. Such thin-walled cannulas provide a greater cross-sectional area than do thicker walled tubes, thereby facilitating flow therethrough.

The illustrated distal end assembly includes a balloon member 21 which is made of a material suitable for a dilatation balloon and in accordance with an appropriate molding approach for that material. The balloon member 21 is securely attached to an outer body tube 22, which outer body tube is attached at its other end to the transition assembly 15. Distal end assemblies can incorporate dual-lumen tubes, for example. The illustrated distal end assembly has a so-called coaxial structure. This coaxial structure includes the outer body tube 22 and an inner body tube or guidewire lumen 23. This type of coaxial structure is generally known. A distal leg portion 24 of the balloon is secured to a distal portion of the inner body tube. The distal end assembly 14 terminates in a distal tip 25. A typical distal end assembly has a length of several centimeters, for example between about 20 cm and about 30 cm.

Distal end assembly 14 also includes a guidewire port 26 at its proximal end. The inner body tube is positioned at this guidewire port so that its proximal opening 27 accommodates a guidewire 28. It will be appreciated that, during use of the illustrated catheters and guidewire, the guidewire lumen 23 and thus the balloon dilatation catheter 11 will be slidably moved with respect to the guidewire, after the quidewire has been inserted to the desired location within the vascular system or the like. Operation of the equipment in this regard is generally known.

Referring to the illustrated transition assembly 15, it incorporates a coil member 31. This coil member is typically helically wound and can be constructed of flat ribbon wire or wire that is generally round in cross-section. The flat ribbon cross-section is preferred. Generally speaking, the coil member 31 can be made of materials such as those which are suitable for the proximal cannula 13. Stainless steel is particularly preferred. Coil member 31 is preferably wound so as to provide a very small gap between adjacent turns of the coil. A gap of about 0.0005 inch about 0.01 mm), typically not more than about 0.001 inch (about 0.025 mm), is typical. This minimizes the risk of coil turn overlap as the coil bends when passing through a curved path. Also possible is a closed pitch structure wherein there are substantially no gaps between adjacent turns of the coil. Whatever gap arrangement is provided, it is important that the overall transition assembly retains adequate torsional and column strengths so that twisting, pushing and pulling forces imparted onto the transitional assembly 15 by the proximal cannula 13 will not cause kinking or permanent twisting of the transitional assembly.

Included in this regard is a consideration of the transition tube 32. Typically, this tube is made of a polymer material. If the tube has good strength attributes, then a less-rigid coil can be provided, including one having a round cross-section and/or having turns which are somewhat spaced apart. Whatever the precise structure utilized, the transitional assembly 15 provides a flexible transition between the generally rigid proximal cannula and the generally flexible distal end assembly.

With more particular reference to the transition tube 32, it is preferred that the inner diameter of the tube closely conforms to the outer diameter of the coil member 31, while allowing sliding between these surfaces of the coil and tube so they slidably engage each other during bending along a curve of the inserted guiding catheter. In the illustrated embodiment, the coil member has a tapered location 33, and the transition tube 32 has its own generally correspondingly shaped and sized tapered location 34. Generally speaking, in making the transition assembly 15, the coil member 31 is wound on a mandrel by means of a coil winder such that its outer diameter is somewhat less than the inner diameter of the tubing for preparing the transition tube 32. The mandrel-supported wound coil is inserted into the inner diameter or lumen of the tubing, and the mandrel is removed.

In the assembly of the coil member 31 and the transition tube 32, the tube is assembled onto the cannula 13 to form a seal area generally designated at 35. In the illustrated embodiment, the proximal end 36 of the transition tube is sealed onto the distal end of the proximal cannula 13. The assembly can be practiced by suitable means including the use of adhesives and/or heat or other suitable procedure or means. Similarly, a distal end 37 of the transition tube 32 extends beyond the distal end of the coil member 31, and this distal end 37 is secured to the proximal end portion of the distal end assembly 14 at a seal area, generally designated at 38. Conveniently, the guidewire port 26 is formed when the proximal end portion of the guidewire lumen 23 is sealed between the distal end portion 37 of the transition tube and the proximal end portion of the outer body tube 22.

In the preferred embodiment, the formation of this seal area 38 is facilitated by having the outer body tube 22 and the transition tube 32 made of materials which are readily heat sealed together. The outer body tube can be made, for example, of a nylon material or of a polyamide material, such as an extruded nylon homopolymer or copolymer or blend of hoiuopolymer and copolymer In the preferred embodiment, at least a portion of the outer surface of the transition tube 32 is made of a nylon material and can be made of the same nylon material or polyamide material as the material out of which the outer body tube 22 is made.

Preferably, at least a portion of the inner surface of the transition tube 32 can be made of a material such as a polyethylene which more readily bonds to the proximal cannula than does a polyamide or nylon material. In the preferred arrangement, the cannula is made of stainless steel, and the outer body tube 22 is made of nylon 12. In order to accommodate these divergent materials, the transition tube 32 is preferably made of two different materials. The preferred manner of accomplishing this desired result is to have the transition tube be a coextrusion. The exemplified coextrusion provides an inner surface of polyethylene, which bonds well to stainless steel, and an external surface of a nylon 12 material or other material which readily bonds to the distal end assembly.

A typical guidewire lumen 23 will accommodate a guidewire 28 having an outer diameter of 0.0014 inch (0.036 mm) when the dilatation catheter is of the PTCA type. When the catheter is, for example, of the PTA type, the guidewire lumen will accommodate a guidewire of a larger outer diameter, usually on the order of 0.0018 inch (0.046 mm). When the coil member 31 is made of a flat stainless steel wire, the thickness of the flat wire will vary between about 0.001 inch and about 0.005 inch (about 0.025 Am to about 0.13 mm), preferably between about 0.002 inch and about 0.004 inch (about 0.05 mm to about 0.1 mm).

FIG. 6 depicts an alternative embodiment for the transition assembly. In this embodiment, the coil member 31 is sandwiched between the transition tube members. An inner transition tube 39 is provided in addition to the outer transition tube 32a. In this instance, the outer transition tube 32a can be especially thin in view of the provision of the inner transition tube 39 as well. With this arrangement, the coil member 31 is sandwiched between the transition tubing.

FIG. 2 illustrates a coil member 31 which incorporates a distally directed extension 41 which helps to protect and strengthen the proximal end portion of the distal end assembly 14 without unduly stiffening the area of joining between the transition assembly and the distal end assembly, including the seal area 38. Typically, this extension 41 is formed by leaving uncoiled a distal portion of the wire from which the coil is wound. This single-piece manner of providing the coil member and the extension avoids any assembly needs, for example. Provision of the distally directed extension 41 also assists in avoiding kinking at this joining location where the relatively thick seal area 38 is directly adjacent to thinner tubing lengths. It is also possible to provide the distally directed extension at the general location of extension 41 and which is assembled onto the transition assembly, such as by welding. Such a distally directed extension can be of a tapered variety which reduces in thickness in the distal direction. Alternatively, additional tubing components could be added in this general area.

Typically, the transition assembly has a total length of between about 10 cm and about 35 cm, preferably between about 12 cm and about 20 cm. The length of the coil member 31 can range between about 5 cm and about 30 cm, preferably between about 8 cm and about 18 cm.

It will be appreciated by those skilled in the art that the guiding catheter 16 and the balloon dilatation catheter 11 can comprise a combination of catheters which are used during balloon dilatation procedures such as angioplasty, typically in association with a guidewire 28. with the present invention, the interaction of this combination of catheters is rendered more beneficial to the physician practicing a dilatation and/or angioplasty procedure. Without the transition assembly discussed in accordance with the present invention, there is a tendency for difficulties to arise when attempting to pass the balloon dilatation catheter through the guiding catheter at a location where the guiding catheter has a tight curve at a location along its length when within the vascular system and/or heart.

An approach which does not follow the transition of the present invention incorporates a stiffening wire at a transition location of a balloon dilatation catheter. When that stiffening wire takes a bend (such as in the aortic arch) it imparts a force on the guiding catheter due to the resistance to bending which is exhibited by such a stiffening wire. This force has a tendency to cause the guiding catheter to dislodge from a desired location, such as from the atrium. The transition assembly of the present invention is able to navigate such a tight bend or curve more easily and thus imparts a much lower force onto the wall of the guiding catheter. This is a relatively low force which is substantially lower than that for a catheter having a stiffening wire at the transition location rather than the transition assembly of the present invention.

It will be understood that the embodiments of the present invention which have been described are illustrative of some of the applications of the principles of the present invention. Various modifications may be made by those skilled in the art without departing from the true spirit and scope of the invention.

We claim:

1. A balloon dilatation catheter comprising:
   an elongated, high-strength proximal cannula having a proximal end, a distal end, and a lumen therethrough;
   a generally tubular distal end assembly having a guidewire passage lumen, a balloon member, and an inflation lumen in fluid passing communication with said lumen of the proximal cannula, said inflation lumen opening into said balloon, said distal end assembly having a flexibility greater than that of the proximal cannula; and
   a coil transition assembly which is positioned between and which longitudinally connects said distal end assembly to said proximal cannula and provides flexible bending strain relief thereat, said coil transition assembly including a coil member having an external surface and a transition tube engaging said external surface of the coil member, said transition tube having an axial length at least as long as that of the coil member.

2. The dilatation catheter in accordance with claim 1, wherein said coil member of the transition assembly is a ribbon wire helically wound into said coil member.

3. The dilatation catheter in accordance with claim 1, wherein said coil member of the transition assembly is a wire of circular cross-section helically wound into said coil member.

4. The dilatation catheter in accordance with claim 1, wherein said coil member includes a plurality of turns which are closely spaced from each other so as to provide a closely gapped coil.

5. The dilatation catheter in accordance with claim 2, wherein said coil member includes a plurality of turns which are closely spaced from each other so as to provide a closely gapped coil.

6. The dilatation catheter in accordance with claim 1, wherein said transition tube of the coil transition assembly extends proximally beyond the proximal end of the coil member and is secured to the distal end of the proximal cannula.

7. The dilatation catheter in accordance with claim 1, wherein a distal end portion of the transition tube extends beyond the distal end of the coil member and is secured to said distal end assembly.

8. The dilatation catheter in accordance with claim 6, wherein a distal end portion of the transition tube extends beyond the distal end of the coil member and is secured to said distal end assembly, wherein said transition tube has an internal surface and an external surface, and wherein said distal end of the proximal cannula is secured to said inside surface of the transition tube, while said proximal end of the distal end assembly is secured to said outside surface of the transition tube.

9. The dilatation catheter in accordance with claim 8, wherein said transition tube is a coextruded tube having an inner surface of a material which is readily bondable to said proximal cannula and having an outer surface which is readily bondable to said distal end assembly.

10. The dilatation catheter in accordance with claim 1, further including a guidewire port generally at a location at which said coil transition assembly is secured to said distal end assembly.

11. The dilatation catheter in accordance with claim 1, further including a distally directed extension from said coil member, said extension being between said coil member and a proximal portion of said distal end assembly.

12. The dilatation catheter in accordance with claim 11, wherein said distally directed extension is a generally axially directed member which is a substantially straight length of wire integral with a distal end portion of the coil member.

13. The dilatation catheter in accordance with claim 11, wherein said distally directed extension is in engagement with said proximal portion of the distal end assembly.

14. A combination balloon dilatation catheter and guiding catheter, comprising:
   a guiding catheter having a length suitable for dilatation procedures, the guiding catheter having a distal tip portion and a guiding lumen with an inner diameter, said distal tip portion having an opening therethrough;
   a balloon dilatation catheter having a series of components, each with an outer diameter smaller than the inner diameter of the guiding catheter so as to permit longitudinal sliding of said balloon dilatation catheter with respect to said guiding catheter and out of said opening of its distal tip portion, said series of components of the dilatation catheter being:
   an elongated, high-strength proximal cannula having a proximal end, a distal end, and a lumen therethrough;
   a generally tubular distal end assembly having a guidewire passage lumen, a balloon member, and an inflation lumen in fluid passing communication with said lumen of the proximal cannula, said inflation lumen opening into said balloon, said distal end assembly having a flexibility greater than that of the proximal cannula; and
   a coil transition assembly which is positioned between and which longitudinally connects said distal end assembly to said proximal cannula and provides flexible bending strain relief thereat, said coil transition assembly including a coil member having an external surface and a transition tube engaging said external surface of the coil member, said transition tube having an axial length at least as long as that of the coil member.

15. The combination in accordance with claim 14, wherein said coil member of the transition assembly is a ribbon wire helically wound into said coil member.

16. The combination in accordance with claim 14, wherein said coil member includes a plurality of turns which are closely spaced from each other so as to provide a closely gapped coil.

17. The combination in accordance with claim 15, wherein said coil member includes a plurality of turns which are closely spaced from each other by between about 0.01 mm and about 0.025 mm so as to provide a closely gapped coil.

18. The combination in accordance with claim 14, wherein said transition tube of the coil transition assembly extends proximally beyond the proximal end of the coil member and is secured to the distal end of the proximal cannula.

19. The combination in accordance with claim 18, wherein a distal end portion of the transition tube extends beyond the distal end of the coil member and is secured to said distal end assembly, wherein said transition tube has an internal surface and an external surface, and wherein said distal end of the proximal cannula is secured to said inside surface of the transition tube, while said proximal end of the distal end assembly is secured to said outside surface of the transition tube.

20. The combination in accordance with claim 14, further including a guidewire port generally at a location at which said coil transition assembly is secured to said distal end assembly.

21. The combination in accordance with claim 14, further including a distally directed extension from said coil member, said extension being between said coil member and a proximal portion of said distal end assembly.

22. The combination in accordance with claim 21, wherein said distally directed extension is a generally axially directed member which is a substantially straight length of wire integral with a distal end portion of the coil member.

23. The combination in accordance with claim 21, wherein said distally directed extension is in engagement with said proximal portion of the distal end assembly.

24. The combination in accordance with claim 19, wherein said transition tube is a coextruded tube having an inner surface of a material which is readily bondable to said proximal cannula and having an outer surface which is readily bondable to said distal end assembly.

25. A procedure for balloon dilatation, comprising the steps of:
providing a guiding catheter having a length suitable for dilatation procedures, the guiding catheter having a distal tip portion and a guiding lumen with an inner diameter and an opening therethrough;
providing a balloon dilatation catheter having a series of components, each with an outer diameter less than the inner diameter of the guiding lumen, said series of components of the balloon dilatation catheter being an elongated high-strength proximal cannula, a generally tubular distal end assembly having a balloon member, and a coil transition assembly therebetween, the coil transition assembly having a coil surrounded by a transition tube;
inserting said guiding catheter to a selected position within the vascular system of a patient so that the tip of the guiding catheter is positioned near a site intended for dilatation treatment, while a portion proximal of its distal tip is tightly curved;
slidably positioning said balloon dilatation catheter into and with respect to the guiding catheter inserted within the vascular system, said slidably positioning including allowing the distal end assembly to pass through and at least partially out of the opening of the guiding catheter distal tip portion while the transition tube of the coil assembly engages an inside surface of the guiding catheter where it is tightly curved and the coil bends therewithin; and
during the slidably positioning step, imparting a force on the guiding catheter by the coil which is so low as to avoid dislodgement of the guiding catheter from its said selected position.

26. The procedure in accordance with claim 25, wherein during said slidably positioning step, the coil flexes to the configuration of a curve which substantially corresponds to the inside surface of the guiding catheter where it is tightly curved.

27. The procedure in accordance with claim 25, wherein during said slidable positioning step, the coil and transition tube assembly flexes to the configuration of a curve which substantially corresponds to the inside surface of the guiding catheter where it is tightly curved.

28. The dilatation catheter in accordance with claim 1, wherein said coil member has an internal surface, and said coil transition assembly further includes an inner transition tube engaging said internal surface of the coil said internal transition tube having an axial length of at least as long as that of the coil member.

29. The combination in accordance with claim 14, wherein said coil member has an internal surface, and said coil transition assembly further includes an inner transition tube engaging said internal surface of the coil member, said internal transition tube having an axial length of at least as long as that of the coil member.

* * * * *

UNITED STATES PATENT AND TRADEMARK OFFICE
CERTIFICATE OF CORRECTION

PATENT NO : 6,036,670
DATED : March 14, 2000
INVENTOR(S) : Lalith Hiran Wijeratne, Luis Alberto Davila and Marco Aurelio Nino It is certified that error appears in the above-identified patent and that said Letters Patent are hereby corrected as shown below:

On the Cover Page, under "References Cited, U.S. Patent Documents" please include
  Pat. No. 4,917,666   4/1990   Solar, et al.
  Pat. No. 5,156,594   10/1992  Keith
On the Cover Page under "References Cited, Foreign Patent Documents" include
  0 608 853 A2   3/1994    EPO
  0 715 863 A2   12/1996   EPO
  93/15786       8/1993    PCT
  95/24236       9/1995    PCT
On the Cover Page, in the ABSTRACT, on the last line, delete "catheterby" and insert --catheter--.
Col. 2, line 25, delete "quidewire" and insert --guidewire--; line 63, after "Another" insert --object--.
Col. 3, line 19, after "invention" insert --is--.
Col. 4, line 10, delete "Nitinold" and insert --Nitinol --; line 61, delete "quidewire" and insert --guidewire--.
Col. 5, line 6, "inch about" should read --inch (about)--; line 63, delete "hoiuopolymer" and insert --homopolymer--; line 63, insert a period --.-- after "copolymer".
Col. 6, line 23, delete "Am" and insert --mm--; line 63, "with the present" should read --With the present--.
Col. 10, line 41, "coil said" should read --coil member, said--.

Signed and Sealed this

Seventeenth Day of April, 2001

*Attest:*

NICHOLAS P. GODICI

*Attesting Officer*   Acting Director of the United States Patent and Trademark Office